US00PP07832P

United States Patent [19]

DeLeon

[11] Patent Number: Plant 7,832

[45] Date of Patent: Mar. 17, 1992

[54] *AECHMA FASCIATA* CULTIVAR 'DELEON'

[75] Inventor: Nat DeLeon, Miami, Fla.

[73] Assignee: DeLeon's Bromeliad World, Inc., Goulds, Fla.

[21] Appl. No.: 544,111

[22] Filed: Jun. 22, 1990

[51] Int. Cl.[5] ..... A01H 5/00

[52] U.S. Cl. ..... Plt./88

[58] Field of Search ..... Plt./88, 88.8

*Primary Examiner*—Howard J. Locker

*Attorney, Agent, or Firm*—Cushman, Darby & Cushman

[57] ABSTRACT

A new and distinct cultivar of *Aechmea fasciata* substantially as herein shown and described, characterized as to novelty by the unique combination of the spineless habit of the leaves and the inflorescence bracts, and also possessing leaves which are densely white lepidote throughout with trichomes concentrated in bands.

3 Drawing Sheets

BACKGROUND OF THE INVENTION

My present invention is that of a new and distinct cultivar of *Aechmea fasciata* which is the result of crossing two unpatented and distinct varieties of *Aechmea fasciata.*

Since 1826 when *Aechmea fasciata* was first introduced into horticulture, it has become the most popular and most widely sold of all bromeliads. Predominating among commercially grown *Aechmea fasciata* plants are those having dense white trichomes on the leaf surface, generally in visually striking barred patterns, giving a silvery appearance to the plants. These plants all bear sharp spines along the leaf edges. Approximately 15 years ago, an odd form of *Aechmea fasciata* of undetermined origin was introduced into the United States by the nursery Fantastic Gardens of Miami, Fla. This odd form differed from all other known varieties of *Aechmea fasciata* in that both the leaves and the bracts of the inflorescence were spineless. However, this form was not considered to be of commercial value because the leaves of the plant, both upper and lower surfaces, were dark green with few dense white trichomes on the leaf surface. As a result, the Fantastic Gardens form did not possess the striking, silvery appearance characterizing commercially accepted plants. Also, this form possessed leaves which were more narrow than the typical commercial plants of today. Plants of the Fantastic Gardens form were propagated only vegetatively through the division of the suckers produced at the base. All attempts to self-pollinate this form failed continually.

In 1986 I decided to cross-pollinate the Fantastic Gardens spineless form and the typical, commercially produced *Aechmea fasciata* having spines. From a thousand or so seeds sown, six of the seedlings showed a spineless leaf character. These were grown in cultivated places initially at Miami, Fla., and more recently at Goulds, Fla. They were grown under the same conditions as all other *Aechmea fasciata* plants that were being grown to be sold commercially, including the same potting mix, the same watering and fertilizer treatment, and subjected to the same growing temperatures. When the plants flowered, they showed the same spineless character of the inflorescence bracts as was possessed by the Fantastic Gardens spineless form. Of these six plants, one was selected by me as having the best combination of wide leaves bearing concentrated bands, or barring, of dense white trichomes presenting a striking silvery appearance and large inflorescence. It has been denominated *Aechmea fasciata* 'DeLeon'. I have reproduced it asexually at Goulds, Fla., by division of basal suckers, with the characters remaining true to type. It has now proved to be suitable to asexual propagation by means of tissue culture.

SUMMARY OF THE INVENTION

My invention can be immediately distinguished from all commercially grown *Aechmea fasciata* varieties in that the leaves are completely devoid of spines and that both the primary and floral bracts of the inflorescence are also spineless.

My invention also differs from its nearest look-alike, the original Fantastic Gardens spineless *Aechmea fasciata* in having broader leaves, 8–10 cm. wide compared to 5–7 cm. in the Fantastic Gardens form; and in having leaves that are densely white lepidote throughout with trichomes concentrated in bands, as opposed to leaves that are sparsely white lepidote with trichomes not heavily concentrated in bands.

BRIEF DESCRIPTION OF THE DRAWINGS

The accompanying photographs clearly depict the new variety while providing a comparison to its nearest look-alikes.

Sheet 1: shows a typical plant of the present invention, *Aechmea fasciata* 'DeLeon'.

Sheet 2: shows a comparison of a typical spiny leaf (lower leaf) and the new spineless form of *Aechmea fasciata* 'DeLeon'.

Sheet 3: shows a comparison of the upper leaf surfaces of the old Fantastic Gardens spineless form (left) and the new spineless form of *Aechmea fasciata* 'DeLeon'.

DETAILED DESCRIPTION

A botanical description has been prepared by Harry Luther, director of the Bromeliad Identification Center located at the Marie Selby Botanical Gardens in Sarasota, Fla. His description was based on a living plant and was done by visiting the nursery in Goulds, Fla., where the plant has been grown. A voucher specimen (SEL #062132) has been deposited with the Bromeliad Identification Center. The botanical description is as follows:

Plant: Flowering to 48 cm tall with stout 4–6 cm long stolons.

Leaves: Rosulate, 16 to 20 in number, spreading, somewhat recurving, dark green, densely white lepidote throughout with trichomes concentrated in bands.

Leaf:

*Sheaths.*—Broadly elliptic, to 12 cm long, 8 cm wide, entire, somewhat castaneous adaxially.

*Blades.*—Lingulate, rounded and apiculate, to 40 cm long, 8–10 cm wide; entire.

Scape: Erect, to 35 cm long, much exceeding the leaf sheaths, 12 mm in diameter, pink, white floccose.

*Bracts.*—Lanceolate, to 6 cm long, lax, entire, densely pale appressed lepidote, bright pink.

Inflorescence: Densely digitate with 10 to 14 polystichously arranged branches, pyramidal.

Primary bracts: Narrowly triangular, pungent, to 8 cm long, 1.2 cm wide, entire, densely pale appressed lepidote, bright pink.

Spikes: Sessile, each polystichously and densely 7 to 20-flowered.

Floral bracts: Triangular, pungent, to 2 cm long, 1.5 cm wide, pale appressed lepidote, bright pink, entire.

Flowers: Sessile, erect.

Sepals: ⅓ connate, asymmetrical, 11–12 mm long, appressed pale lepidote, pink.

Corolla: Erect, tubular.

Petals: Lingulate, 28–30 mm long, cucculate, basally appendaged with two fimbriate scales, blue fading to dark rose.

Ovary: Ellipsoid, to 6 mm long.

Fruit: Light blue when mature.

Voucher specimen: Deposited at SEL (#062132).

Coloration

As an aid to understanding the coloration of my new variety, its coloration has been observed and compared with color plates from a standard reference work, namely the Munsell Limit Color Cascade (MLCC) published by Munsell Color Company. The observations were made under natural daylight from plants grown under standard polypropylene shadecloth giving 73% shade, which plants had received once per week fertilizing with a liquid fertilizer (20-20-20) injected into the irrigation sprinkler system used for watering them. (The green leaf color can vary according to light exposure and fertilization. Light exposure brighter than 65% shade will bleach the color, and plants not fertilized or fertilized only infrequently will produce foliage of a lighter green. Exposure to light brighter than 65% shade will bleach the color of the inflorescence bracts, particularly during the summer months. Exposure to full sunlight for an hour or more will burn all plant parts.)

Leaves: The underside of leaves is dark green (MLCC No. 21-15), heavily covered with silver-white lepidote trichomes which in many areas completely obscure the green color. The upper leaf surface is dark green (MLCC No. 20-14), with the silver-white trichomes forming prominent bands.

Floral and scape bracts: The flower bracts and scape bracts are light pink (MLCC No. 41-3) at anthesis, deepening to dark pink (MLCC No. 42-5) after all flowers have been spent. Floral bracts and scape bracts are lightly dusted with silver-white trichomes, which become more prominent after flowering.

Flowers: The flower petals are blue (MLCC No. 4-6). The flowers open only slightly and each flower lasts only one day. By the end of the second day, the petals are shriveled and turn gradually to purple (MLCC No. 1-10) in color. By the third day, the petals turn black. A new series of from 3 to 12 flowers emerge daily until blooming is concluded, resulting in all of these color shades being present.

Additional Distinguishing Characteristics

Plants of the new variety have shown a remarkable resistance to Fusarium Sp., a root rot disease that usually affects at least 10% of a crop of other varieties of *Aechmea fasciata* even when preventative spraying of fungicides is utilized. No significant losses to root rot have been experienced.

As far as is known, no variety of *Aechmea fasciata* is self-fertile. Many attempts at self-pollination of my new variety have met with failure. It will accept pollen from other forms of *Aechmea fasciata* and the pollen of my new variety has proven to be fertile.

My new variety can be artificially induced to bloom without difficulty by treatment with Florel bloom inducer, at the rate of one teaspoon per gallon of water. Commercially acceptable inflorescence color becomes evident in nine to eleven weeks after treatment during the warm summer months, and in eleven to fourteen weeks during the cooler winter months, in the conditions existing in Southern Florida. This is a commercially important factor since many commercially grown bromeliad genera, such as Guzmania, Vriesea and Tillandsia, can require more than twice as long following hormone treatment to initiate flowering.

I claim:

1. A new and distinct cultivar of *Aechmea fasciata* substantially as herein shown and described, characterized as to novelty by the unique combination of the spineless habit of the leaves and the inflorescence bracts, and also possessing leaves which are densely white lepidote throughout with trichomes concentrated in bands.

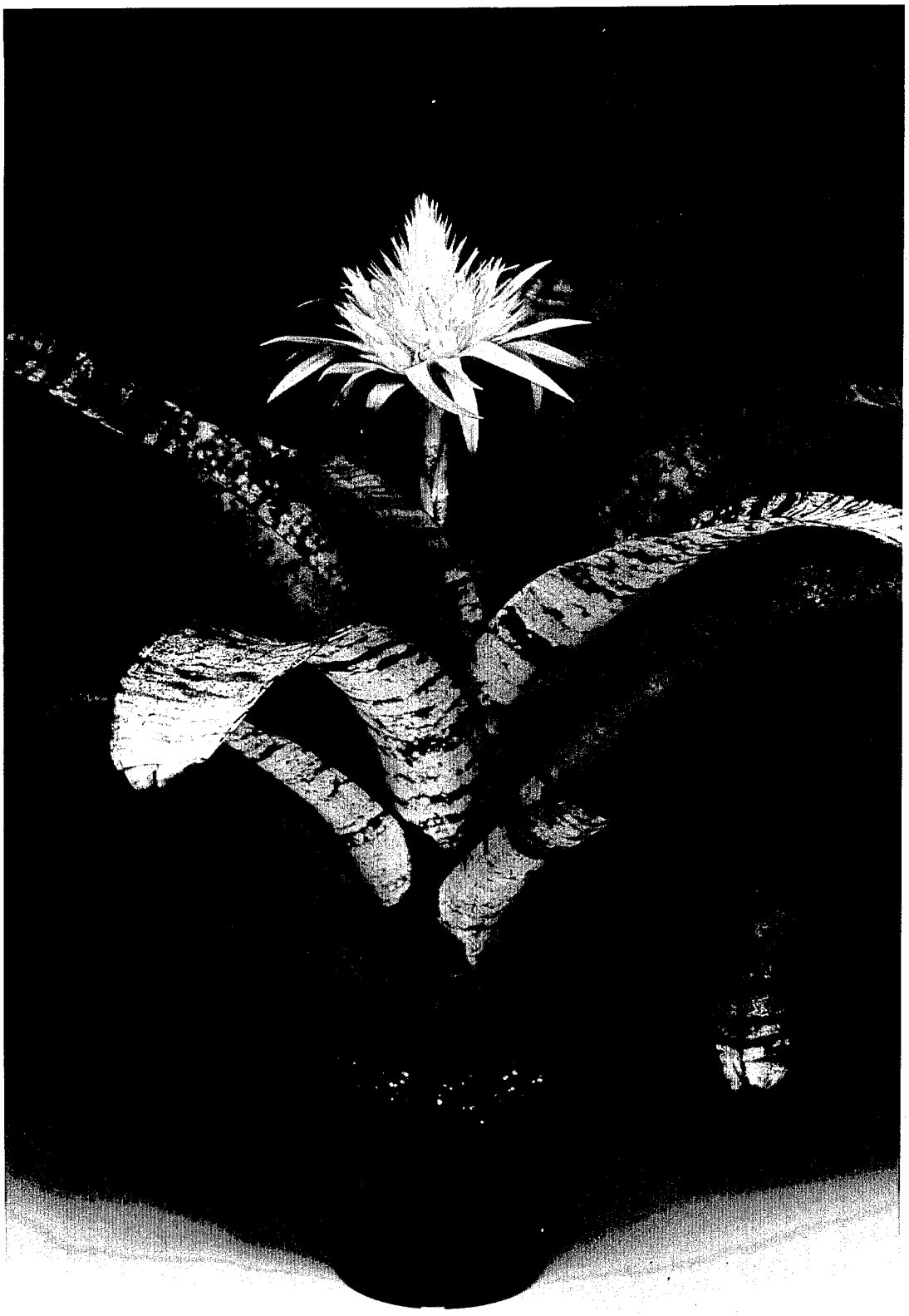

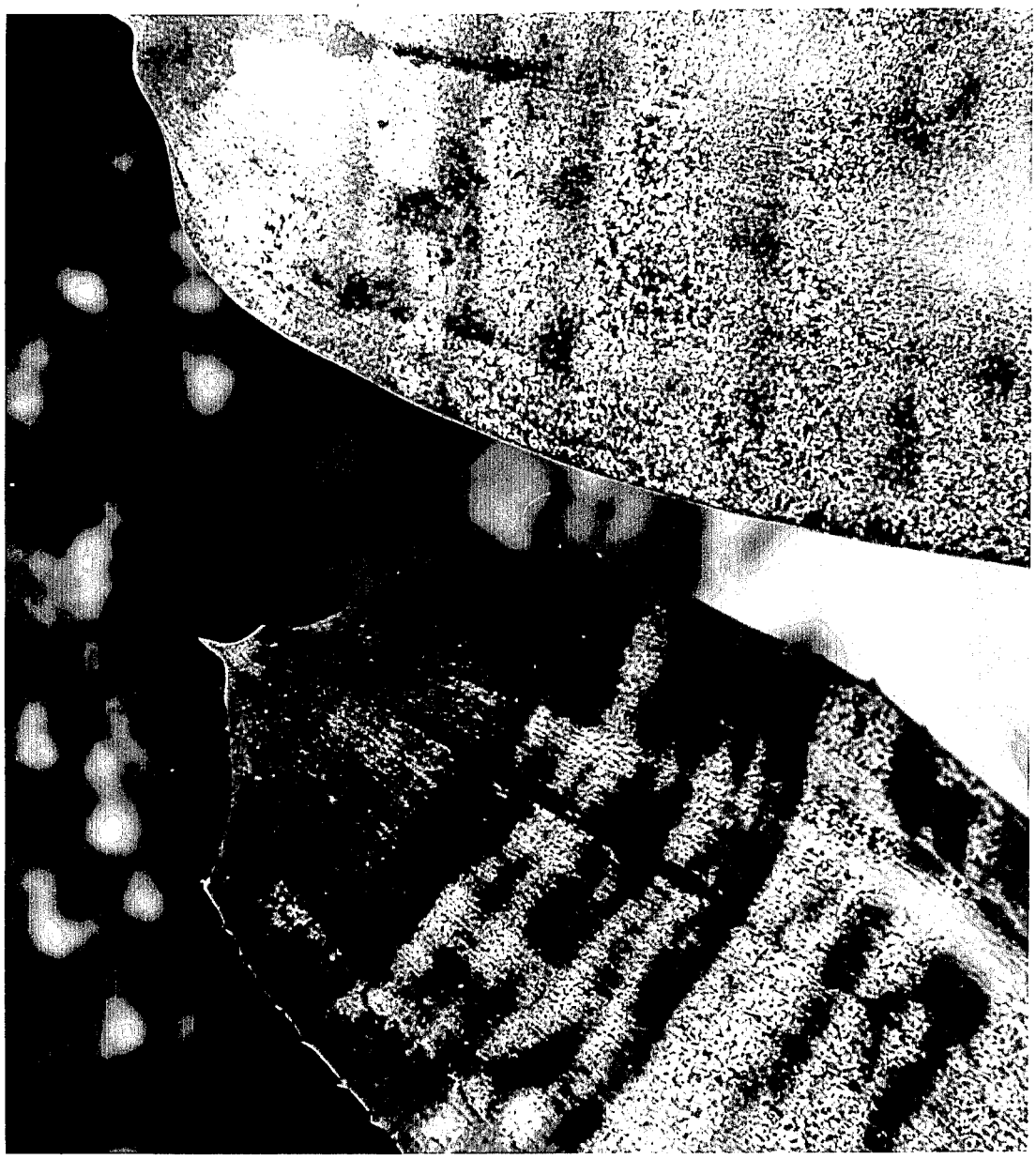

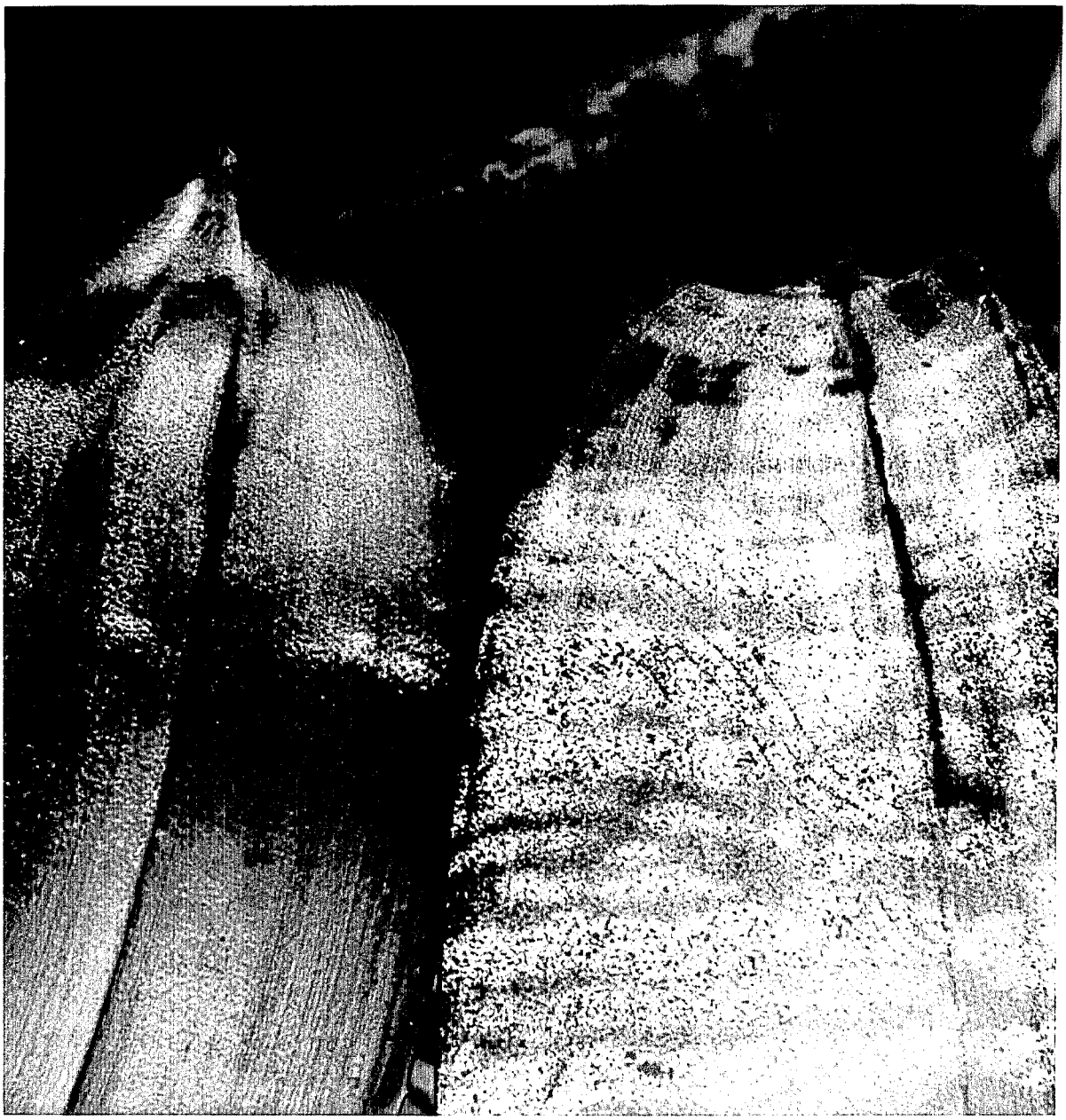

* * * * *